United States Patent
O'Neil et al.

(10) Patent No.: US 6,527,807 B1
(45) Date of Patent: *Mar. 4, 2003

(54) FEMORAL STEM ATTACHMENT FOR A MODULAR KNEE PROSTHESIS

(75) Inventors: Michael O'Neil, West Barnstable; Justin Dye, Mansfield, both of MA (US)

(73) Assignee: Johnson & Johnson Professional, Inc., Raynham, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 40 days.

(21) Appl. No.: 09/150,122

(22) Filed: Sep. 9, 1998

(51) Int. Cl.[7] .................................................. A61F 2/38
(52) U.S. Cl. .................................................. 623/20.15
(58) Field of Search ................................ 623/20, 20.15, 623/20.14, 20.21, 20.36, 26.35, 20.31, 20.27

(56) References Cited

U.S. PATENT DOCUMENTS

| | | | |
|---|---|---|---|
| 4,219,893 A | 9/1980 | Noiles | 3/1.911 |
| 4,301,553 A | 11/1981 | Noiles | 3/1.911 |
| 4,404,691 A | 9/1983 | Buning et al. | 3/1.911 |
| 4,578,081 A | 3/1986 | Harder et al. | 623/22 |
| 4,624,673 A | 11/1986 | Meyer | 623/16 |
| 4,714,471 A | 12/1987 | Grundei | 623/20 |
| 4,790,852 A | 12/1988 | Noiles | 623/18 |
| 4,790,854 A | 12/1988 | Harder et al. | 623/20 |
| 4,822,366 A * | 4/1989 | Bolesky | 623/20 |
| 4,834,758 A | 5/1989 | Lane et al. | 623/18 |
| 4,846,839 A | 7/1989 | Noiles | 623/18 |
| 4,888,021 A | 12/1989 | Forte et al. | 623/20 |
| 4,904,110 A | 2/1990 | Klein | 403/379 |
| 4,936,847 A * | 6/1990 | Manginelli | 623/23 |
| 4,936,853 A | 6/1990 | Fabian et al. | 623/20 |
| 4,944,757 A | 7/1990 | Martinez et al. | 623/20 |
| 4,985,037 A | 1/1991 | Petersen | 623/20 |
| 5,011,496 A | 4/1991 | Forte et al. | 623/20 |
| 5,019,103 A | 5/1991 | Van Zile et al. | 623/20 |

(List continued on next page.)

FOREIGN PATENT DOCUMENTS

| | | | |
|---|---|---|---|
| DE | 0473375 | 2/1929 | 411/398 |
| DE | 1575278 | 5/1978 | A61F/1/03 |
| DE | 781535 | 2/1997 | A61F/2/38 |
| DE | 820739 | 1/1998 | A61F/2/38 |
| EP | 0144667 | 6/1985 | |
| EP | 0307655 | 3/1989 | A61F/2/38 |
| EP | 0531263 * | 6/1992 | 623/20.15 |
| EP | 531263 * | 6/1992 | 623/20.15 |
| EP | 0529408 | 3/1993 | A61F/2/38 |
| EP | 0531263 | 3/1993 | A61F/2/38 |
| EP | 0621019 | 10/1994 | |
| GB | 2259253 | 3/1993 | A61F/2/02 |
| WO | 9709939 | 3/1997 | |

OTHER PUBLICATIONS

Johnson & Johnson Orthopaedics Research & Development "P.F.C.® Modular Knee System Research Data and Laboratory Testing," cover and pp. 8, 36 and 37 (1989).

Primary Examiner—David H. Willse
Assistant Examiner—Alvin Stewart
(74) Attorney, Agent, or Firm—Nutter, McClennen & Fish, LLP (57) ABSTRACT

The present invention provides a knee prosthesis having a femoral component having a pair of spaced apart condylar portions and a boss structure extending between the condylar portions. The boss structure has a top surface that extends generally horizontally in a transverse plane and an opposed inferior surface. The knee prosthesis also includes a stem component having a proximal end and a distal end. The knee prosthesis further includes an attachment nut for securing the stem member to the femoral component.

14 Claims, 8 Drawing Sheets

U.S. PATENT DOCUMENTS

| | | | |
|---|---|---|---|
| 5,057,111 A | 10/1991 | Park | 606/69 |
| 5,127,914 A | 7/1992 | Calderale et al. | 606/65 |
| 5,133,760 A | 7/1992 | Petersen et al. | 623/20 |
| 5,137,535 A | 8/1992 | Keller | 623/20 |
| 5,152,796 A | 10/1992 | Slamin | 623/20 |
| 5,194,066 A | 3/1993 | Van Zile | 623/20 |
| 5,269,784 A * | 12/1993 | Mast | 606/69 |
| 5,290,313 A * | 3/1994 | Heldreth | 623/20 |
| 5,326,359 A | 7/1994 | Oudard | 623/20 |
| 5,330,534 A | 7/1994 | Herrington et al. | 623/20 |
| 5,336,225 A | 8/1994 | Zang | 606/73 |
| 5,370,701 A | 12/1994 | Finn | 623/20 |
| 5,397,360 A | 3/1995 | Cohen et al. | 623/16 |
| 5,405,395 A | 4/1995 | Coates | 623/20 |
| 5,413,605 A | 5/1995 | Ashby et al. | 623/20 |
| 5,556,433 A * | 9/1996 | Gabriel et al. | 623/20 |
| 5,609,641 A | 3/1997 | Johnson et al. | 623/20 |
| 5,683,472 A * | 11/1997 | O'Neil et al. | 623/20 |
| 5,895,428 A * | 4/1999 | Berry | 623/17 |

* cited by examiner

FEMORAL STEM ATTACHMENT FOR A MODULAR KNEE PROSTHESIS

CROSS-REFERENCE TO RELATED APPLICATIONS

Not applicable.

STATEMENT REGARDING FEDERALLY SPONSORED RESEARCH

Not applicable.

FIELD OF THE INVENTION

The invention relates to medical devices, and more particularly to prosthetic joint components.

BACKGROUND OF THE INVENTION

Joint arthroplasty is a well-known surgical procedure by which a diseased and/or damaged natural joint is replaced by a prosthetic joint. A typical knee prosthesis includes a tibial component, a femoral component, a femoral stem assembly, and a patellar component. The femoral component generally includes a pair of spaced apart condylar portions, the superior surfaces of which articulate with a portion of the tibial component. The femoral stem assembly provides lateral stability, and it typically includes a member that is inserted within a reamed intramedullary canal at the distal end of a femur. The stem is typically coupled to the femoral component by a collar and bolt.

Although modular systems can provide an advantageous reduction in joint component inventory, known systems do not fully address the problems associated with variations in intramedullary canal geometry. Specifically, the variations in the morphology of the intermedullary canal often do not match the geometry of the stem, forcing the surgical positioning of the femoral component that is mated to the stem to be determined by considerations other than the shape of the canal.

For example, if the implant geometry does not match the canal geometry, the stem of the implant can contact the cortical wall of the intramedullary canal while the stem is being impacted. This problem can be further complicated when a femoral stem is mated to a sleeve that increases the effective length of the stem so that it is in a bowed portion of the intramedullary canal.

In response to the above problems, a surgeon may be forced to remove the stem (or entire component) and replace it with a stem having a smaller diameter or shorter length, even if the replacement stem is thought to be less suitable than the original stem, but for the improper fit. Also, the surgeon may have to cut notches in the femur to accommodate a shifted femoral component.

Therefore, despite the existence of joint prostheses having modular components, there remains a need for a modular joint prosthesis that has greater versatility to accommodate differing patient anatomy and joint conditions.

BRIEF SUMMARY OF THE INVENTION

The present invention relates to a modular knee joint prosthesis having improved versatility. Components of the modular prosthesis of the invention are able to be used with both right and left side prostheses.

The present invention provides a modular knee prosthesis which includes a femoral component having a pair of spaced apart condylar portions and a boss structure extending between the condylar portions. The boss structure has a top superior surface that extends generally horizontally in a transverse plane and an opposed inferior surface which has a cavity formed therein that terminates in a substantially spherically shaped endwall. The boss structure further includes an aperture which extends between the mounting and securing surfaces of the boss structure. The knee prosthesis further includes a stem component which has a proximal end and a distal end that is mountable through the boss aperture.

A mounting surface is provided which may be either integrated into the stem component or provided as a separate collar component for varying the angulation of the stem component relative to the femoral component. The mounting surface is oriented substantially transverse to a longitudinal axis of the stem member such that the mounting surface and the top surface of the boss structure define a selected mounting angle therebetween. Finally, the knee prosthesis includes an attachment nut having a spherically shaped superior surface for engaging the spherically shaped endwall of the boss structure to secure the stem member to the femoral component.

BRIEF DESCRIPTION OF THE DRAWINGS

A more complete understanding of the present invention and the attendant advantages and features thereof will be more readily understood by reference to the following detailed description when considered in conjunction with the accompanying drawings wherein.

DETAILED DESCRIPTION OF THE INVENTION

Figure 1:
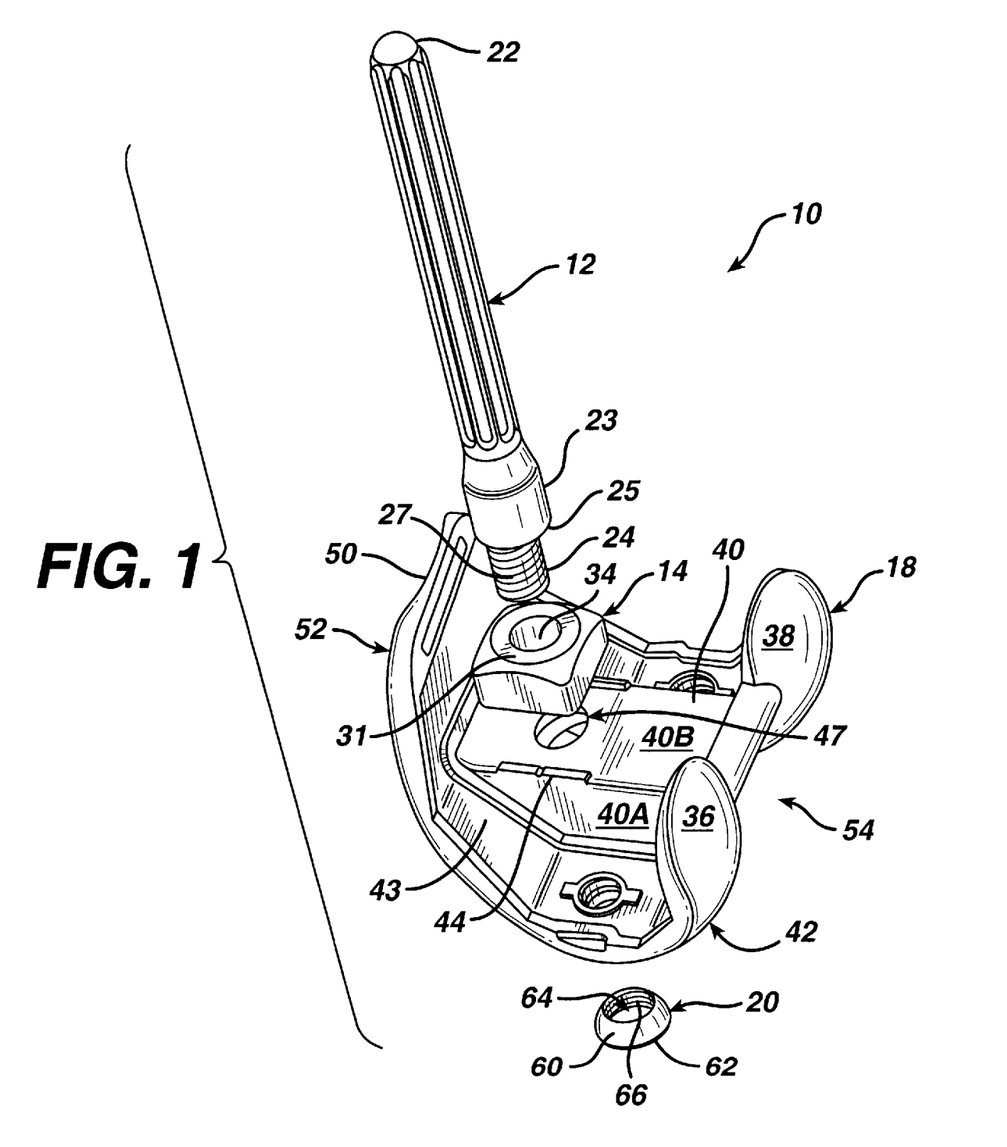
FIG. 1 is an exploded view of a multi-piece prosthetic joint component system.
Figure 2:
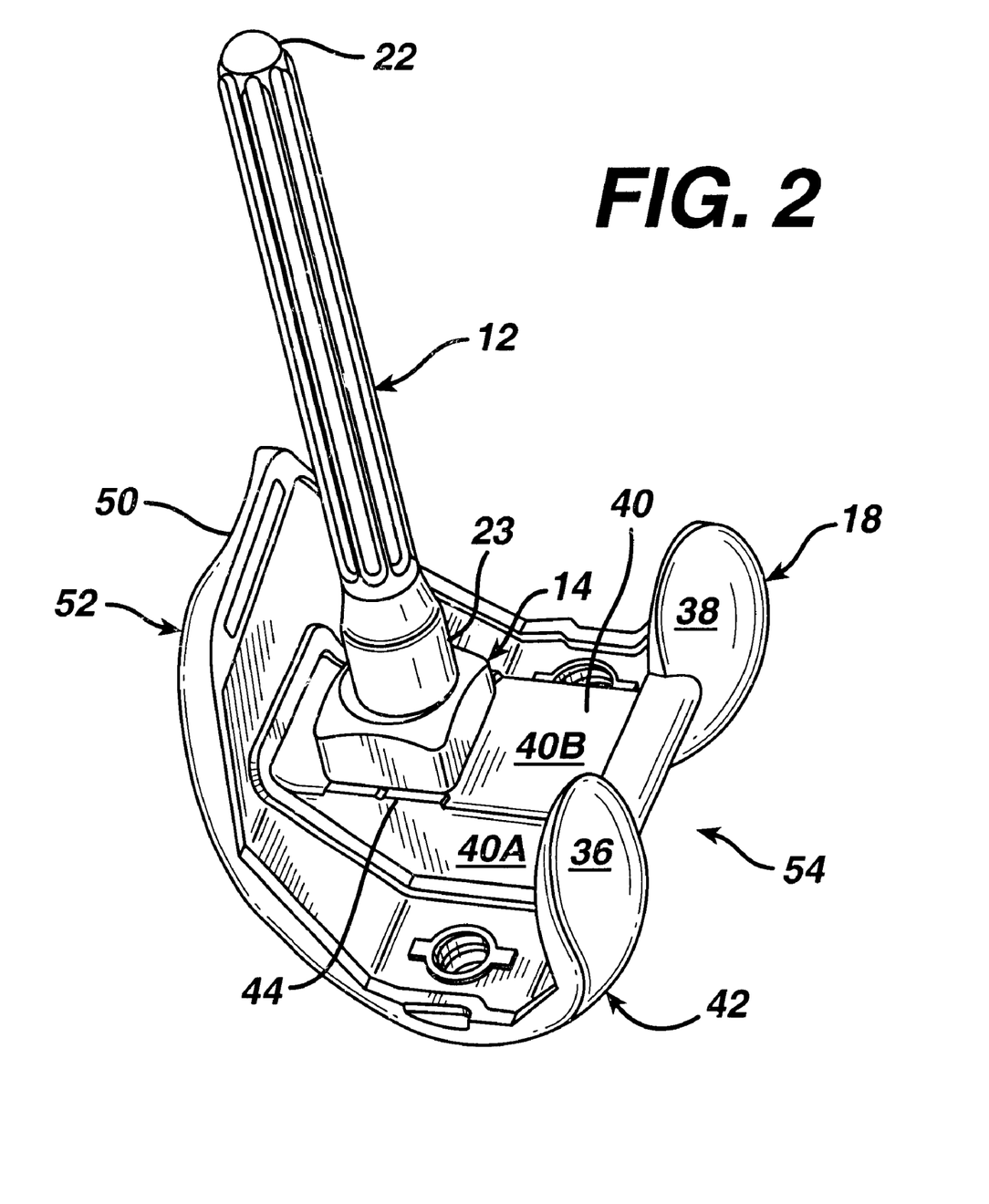
FIG. 2 is an assembled view of the joint component system shown in FIG. 1.
Figure 3A:
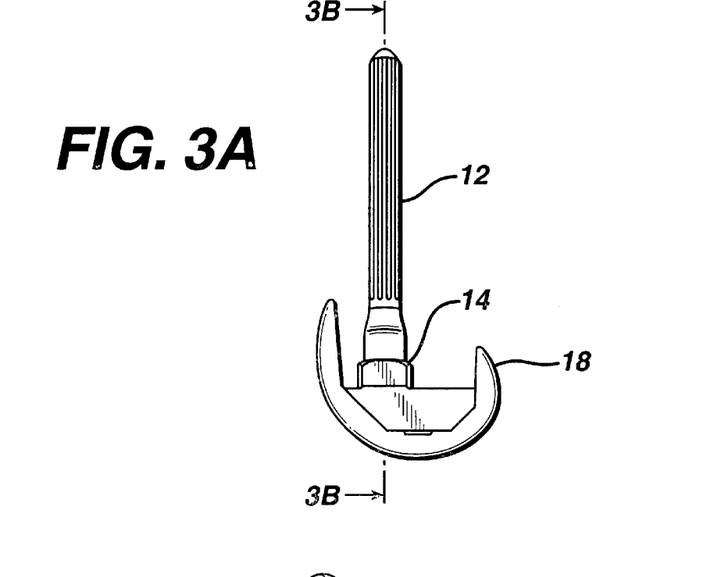
FIG. 3A is a side view of the joint component system of FIG. 1.
Figure 3B:
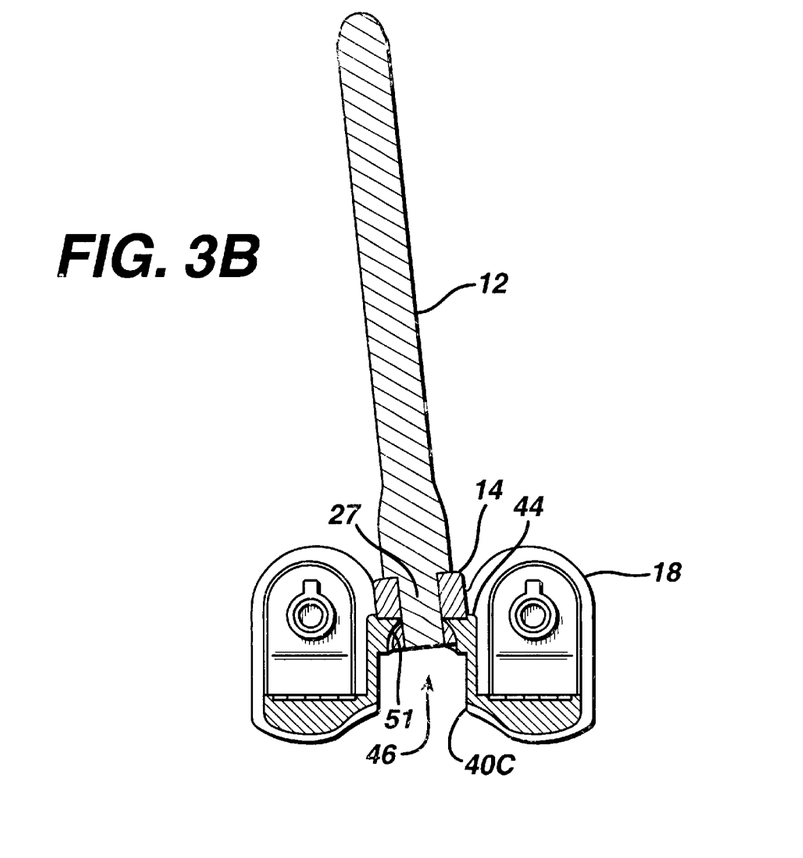
FIG. 3B is a sectional view of the joint component system taken along line 3B—3B in FIG. 3A.

FIG. 1 is an exploded view of a modular prosthetic joint prosthesis 10 that includes a number of modular components including an elongate stem 12, a collar member 14, a femoral component 18, and an attachment nut 20. The construction of the present invention provides several mounting possibilities that are compatible with the various possible orientations of the femoral stem when mounted within the distal portion of the femur.

Referring to FIGS. 1–4B, the stem 12 has a proximal end 22 and a distal end 24 with a bulged portion 23 disposed between the proximal and distal ends 22, 24. The bulged portion 23 includes a distally facing mating shoulder portion 25 adapted for mating with a superior seating surface 31 of collar member 14. The distal end 24 of the stem 12 includes a connector portion 27 which extends distally from the bulged position 23. The connector portion 27 may have threads formed thereon effective to threadably engage the attachment nut 20, as discussed in more detail later herein. In an exemplary embodiment, the connector portion 27 of stem 12 has an outer diameter substantially smaller than the outer diameter as measured at the bulged portion 23. Preferably, the diameter of the proximal end 22 of sleeve 14 is also less than the outer diameter of the bulged portion 23.

Figure 4A:
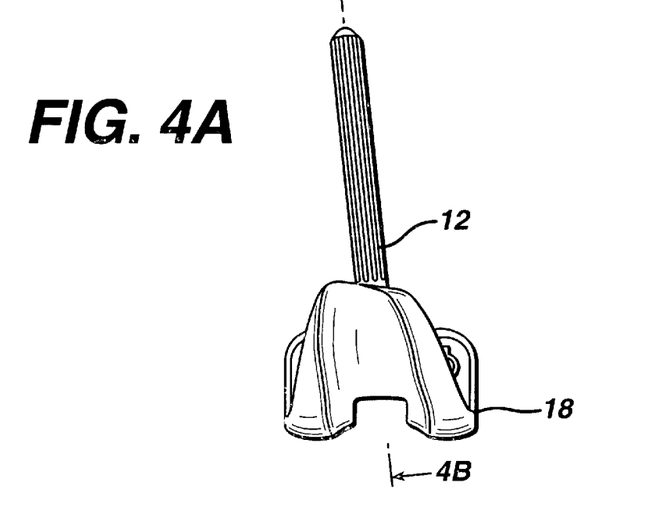
FIG. 4A is a front view of the joint component system of FIG. 1.
Figure 4B:
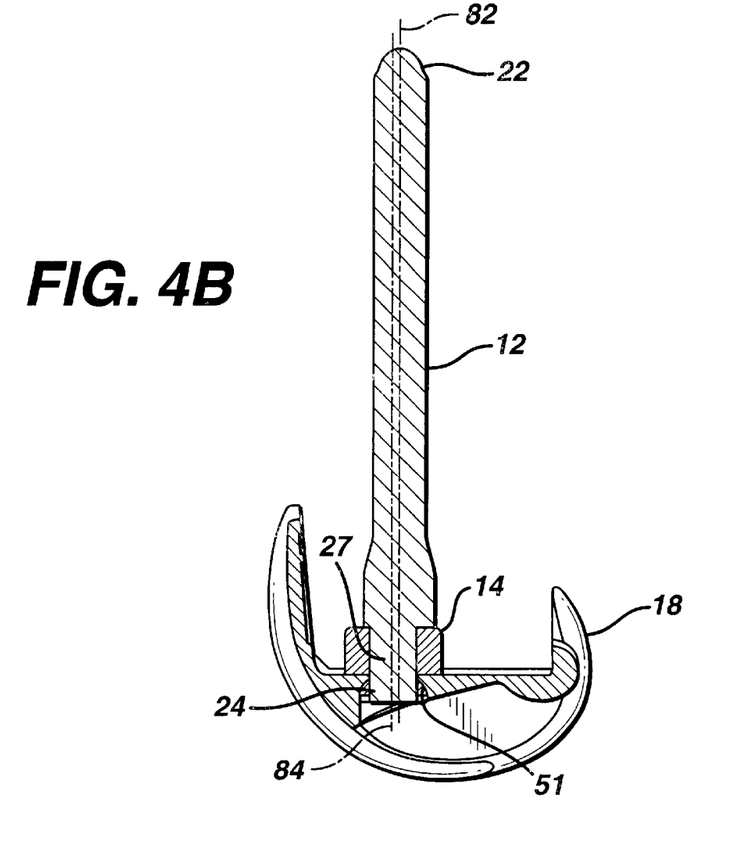
FIG. 4B is a sectional view of the joint component system taken along line 4B—4B in FIG. 4A.

In an exemplary embodiment as shown in FIG. 4B, the stem 12 has a degree of lateral offset between a first longitudinal axis 82 extending through the proximal end 22 and a second longitudinal axis 84 extending through the distal end 24 of stem 12. The lateral offset between the first and second axes 82, 84 can vary depending upon a patient's anatomical requirements, but the offset generally is in the range of 2 to 8 mm. While the embodiment shown and described above allows for offset in either direction of the medial-lateral plane, the embodiment shown in FIGS. 1–4B allows offset placement in the medial-lateral direction, the anterior-posterior direction, and virtually at any position between medial-lateral and anterior-posterior.

With reference to FIGS. 1, 2 and 5A–5B, the collar member 14 has a central body portion 28 that has an outer peripheral surface 29, an inferior boss engaging surface 30 and a superior stem seating surface 31. The shoulder portion 25 of stem 12, when assembled with the collar 14, preferably mates with and engages the stem seating surface 31, which is sized to receive femoral stems having various diameters, including diameters of about 6 to 30 mm.

Figure 5A:
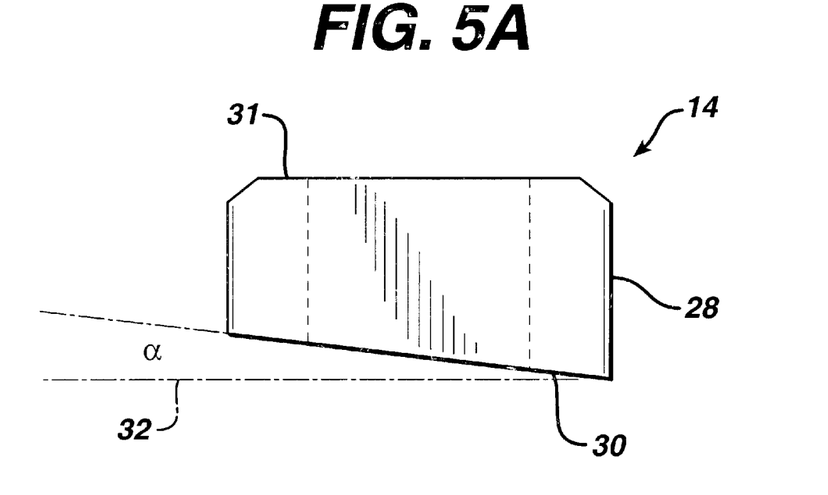
FIG. 5A is a side view of the collar member of FIG. 1.
Figure 5B:
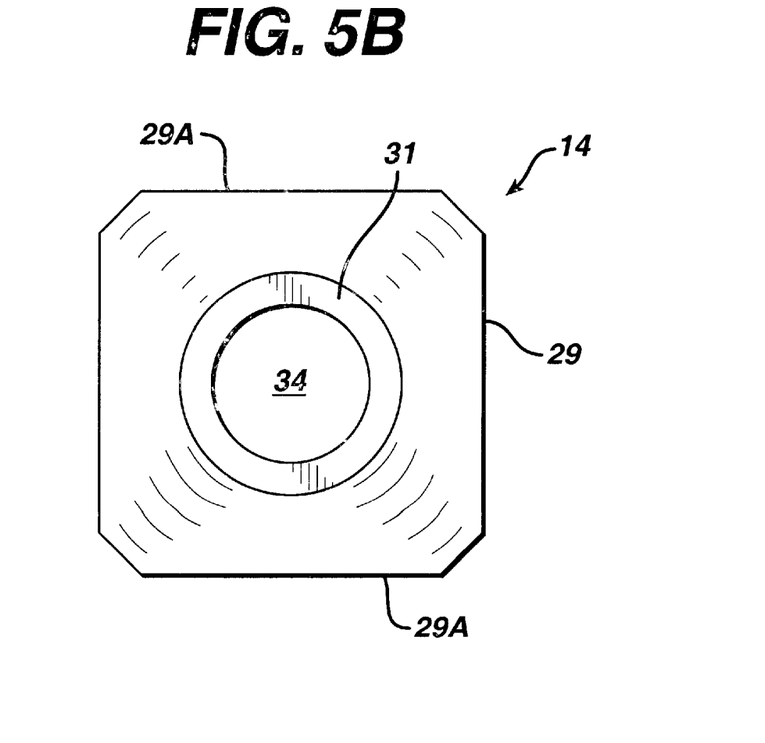
FIG. 5B is a top view of the collar member of FIG. 5A.

The boss engaging surface 30 is preferably canted and forms an angle with a transverse plane 32. The boss engaging surface 30 and a top surface 40B of boss structure 40 which lies in the transverse plane, form a mounting angle (α) when the collar is assembled with the femoral component and engages the boss top surface 40B. The angle (α) is preferably between about 1° and about 15°. According to one practice of the invention, the boss engaging surface 30 can be canted in the anterior-posterior direction to either the anterior or posterior side as measured in the sagittal plane. Likewise, the surface 30 can be canted in the medial-lateral direction to either the medial side or the posterior side as measured in the coronal plane. Preferably, the angle (α) can range between about 1° and about 15° in any direction. This varied collar angulation provides a plurality of stem mounting angles which is compatible with the various possible orientations of the femoral stem when mounted within the distal portion of the femur. Those of ordinary skill in the art readily appreciate that the boss mounting surface 30 can be configured to provide any combination of coronal and sagittal plane angulations that are constrained by the foregoing angle ranges.

The collar 14 can be used with either right or left side knee prostheses. Generally, the collar is positioned such that the angle (α) is to the lateral side of the prosthesis, as measured in the coronal plane. The same collar can be used in either left or right side prosthesis by simply reversing the orientation of the collar on the prosthesis to ensure a lateral angle for the femoral stem 12.

The collar peripheral surface 29 also has at least one pair of opposed flat sides 29A. Flat sides are adapted to engage raised ridges 44 formed on the top surface 40B of boss structure 40. The mating contact between the raised ridges 44 and the flat sides 29A of the collar peripheral surface 29 prevents unwanted rotation of the collar 14 when mounted on the boss top surface 40B. The collar 14 further has a central aperture 34 which receives the distal connector portion end 24 of femoral stem 12.

Referring to FIGS. 1–4B, the femoral component 18 has a pair of condylar portions 36, 38 that are connected by an intercondylar boss or box structure 40. The femoral component 18 also has an articulation surface 42 and an opposed surface 43. Further, the femoral component 16 has an anterior side 52 and a posterior side 54. The anterior side 52 of the femoral component 16 includes a patellar groove 50 within which seats a patellar prosthetic component (not shown). The surfaces 42 of the curved condylar portions 36, 38 articulate with a prosthetic tibial component (not shown) mounted on the head of the tibia, in a manner well known to those of ordinary skill in the art.

The boss structure 40 has a pair of substantially vertical side walls 40A that are connected by a top or superior, seating surface 40B. The boss structure 40 further has a cavity 46 formed within a bottom or inferior surface 40C. The cavity 46 is further defined at one end by curved spherical sidewalls 51 which have a complementary shape to mate with and engage attachment nut 20. Once the prosthesis is assembled, the sidewalls 51 engage attachment nut 20 so that the femoral stem is secured at a desired angulation, as discussed in more detail later herein.

The boss structure 40 further includes an aperture 47 formed thereon which extends between the surfaces 40B, 40C, respectively, of the boss structure 40. The shape of the aperture 47 in the boss structure 40 can be elliptical, oval, spherical, or of any other suitable shape that allows a sufficient amount of translation of the securing bolt shaft when the bolt is mounted within the aperture.

FIG. 1 illustrates the attachment nut 20 useful with the present invention. The nut 20 includes a generally spherical top portion 60 and a bottom portion 62. A central aperture 64 extends between the top and bottom portions 60, 62. Preferably, threads are formed within an inner surface 66 of the nut 20 effective to threadably engage corresponding threads formed on the distal end of the stem 12. The spherical top portion 60 mates with and engages the similarly configured endwall of the femoral boss cavity.

Referring to FIGS. 1–5B, an exemplary modular knee prosthesis utilizing the component described above can be assembled in the following manner. The collar 14 is mounted on the top surface 40B of the boss 40 by aligning and engaging ridges 44 with collar flat sides 29A such that the collar aperture 34 is aligned-with box aperture 47. The stem 12 is mated to the collar 14 by positioning the distal connector portion 27 through collar aperture 34 so that the mating surface or shoulder 25 rests upon the stem seating surface 31 of the collar 14. The distal end 24 of stem 12 is further extended and passed through box aperture 47 such that at least a portion of the connector end 27 protrudes and extends into box cavity 46. The attachment nut 20 is inserted into the boss cavity 46 from the underside of the boss structure to threadably engage the distal connector portion 27 of the stem 12.

In such a configuration, the spherical engaging surface 60 of the attachment nut 20 mates with and engages the similarly configured endwall 51 of the boss cavity 46. The selected shape of the cavity endwall 51 allows the attachment nut 20 to seat within the cavity 46 at an angle that is determined by the collar 14. In such a configuration, the boss mounting surface 30 of the collar 14 determines the stem angulation once the components are assembled together. The threaded connector portion 27 of the distal end of the stem 12 threadably engages the threaded attachment nut 20 and fixedly secures the stem 12 to the femoral component 18. In this axially successive assemblage, the collar is pressure fitted between the stem and boss by the threaded engagement of the stem and nut.

FIGS. 6–9 illustrate a prosthesis system 100 which is a variation of system 10 described in FIGS. 1–5B. System 100 includes the various components present in FIG. 1, including an elongate stem 112, a femoral component 118 and an attachment nut 120.

The stem 112 and femoral component 118 differ slightly from the components described above with respect to FIGS. 1–4B. In this embodiment, the stem 112 allows for the interchanging of stem components having varied angulations to provide a variety of mounting possibilities for the prosthesis. The stem 112 includes proximal and distal ends 122, 124 with a boss engaging surface 130 disposed proximal the distal end of the stem.

Figure 9:
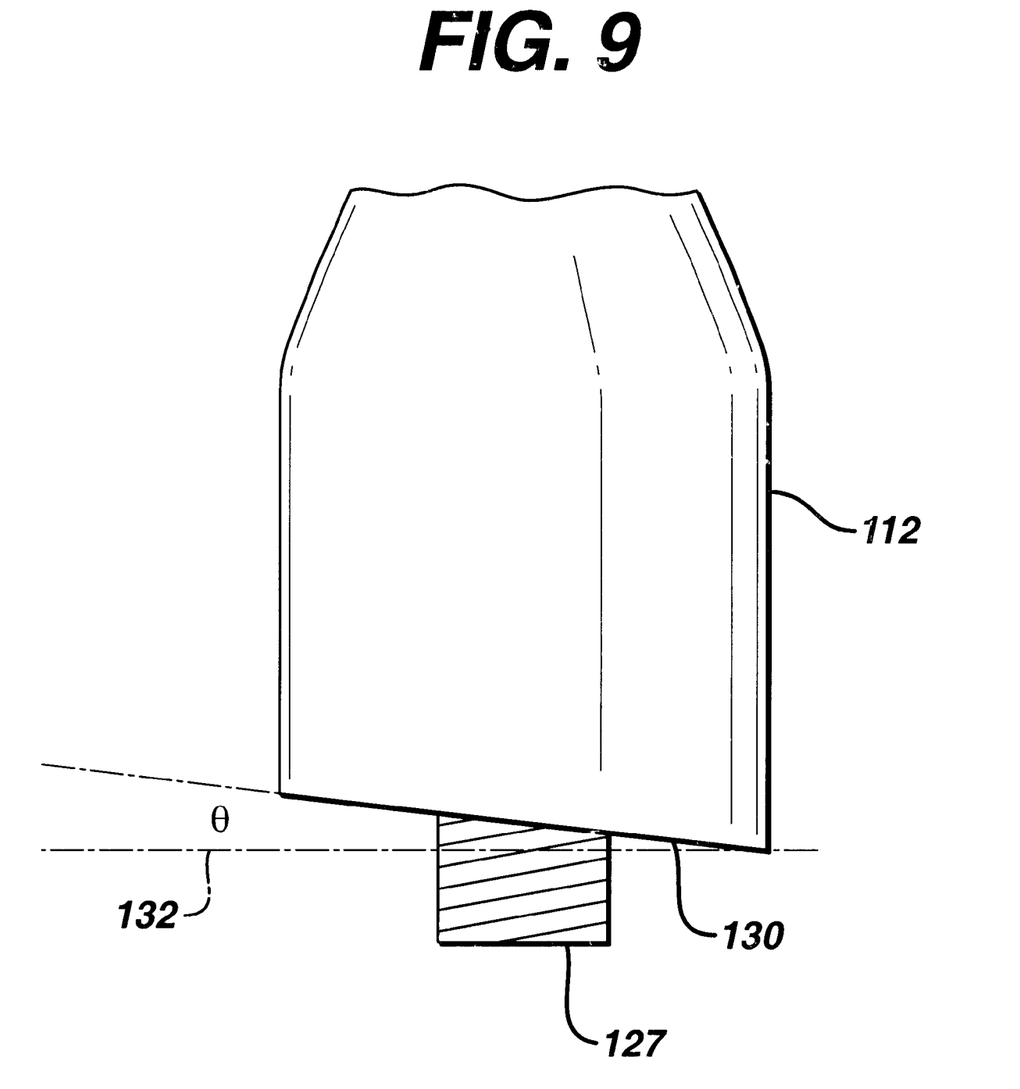
FIG. 9 is a detailed side view of portion A in FIG. 6.

Referring to FIG. 9, the boss engaging surface 130 is preferably canted and forms an angle with the transverse plane 132. The boss engaging surface 130 and the top surface 140B of the boss 140, which lies in the transverse plane, form a mounting angle (θ) when the stem is assembled with the femoral component and engages the boss top surface. The angle (θ) is preferably between about 1° and about 15°. According to one practice of the invention, the boss engaging surface 130 can be canted in the anterior-posterior direction to either the anterior or posterior side as measured in the sagittal plane. Likewise, the boss engaging surface 130 can be canted in the medial-lateral direction to either the medial side or the posterior side as measured in the coronal plane. Preferably, the angle (θ) can range between about 1° and about 15° in any direction. This varied angulation provides a plurality of stem mounting angles which is compatible with the various possible orientations of the femoral stem when mounted within the distal portion of the femur. Those of ordinary skill in the art readily appreciate that the boss mounting surface 130 can be configured to provide any combination of coronal and sagittal plane angulations that are constrained by the foregoing angle ranges.

Figure 6:
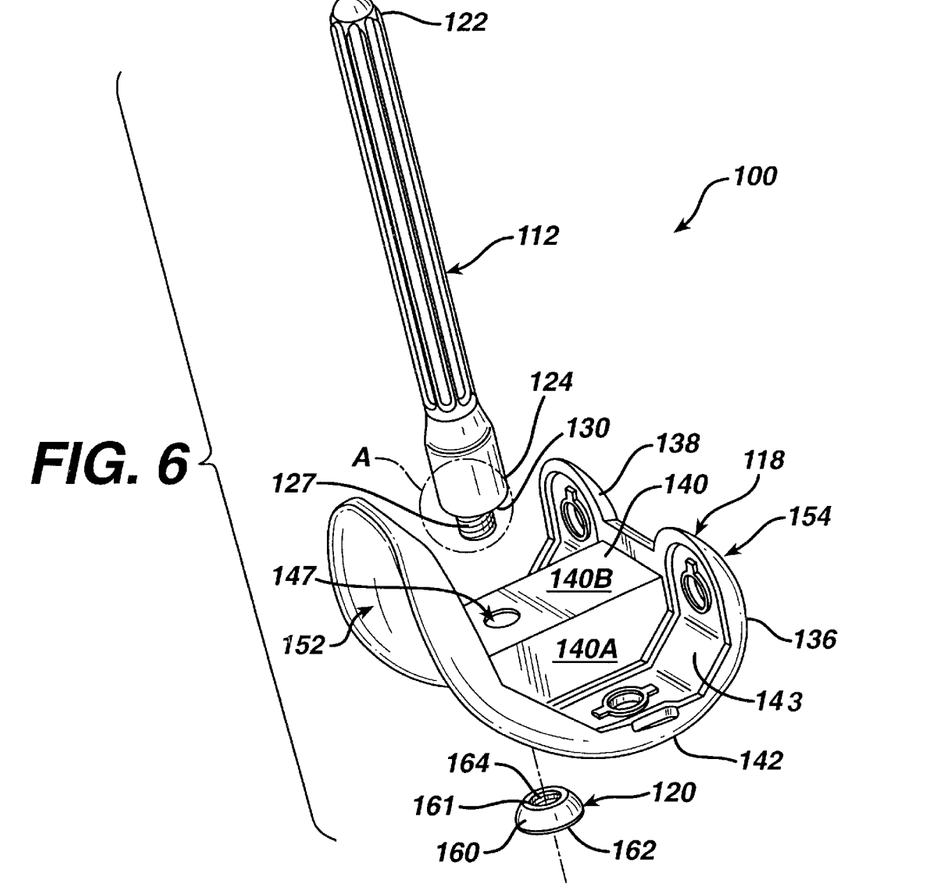
FIG. 6 is an exploded view of an alternative embodiment of the multi-piece prosthetic joint component system.

The stem 112 further includes a connector end portion 127 which extends distally from the boss engaging surface 130. Preferably, the connector end 127 has threads formed thereon effective to threadably engage a corresponding threaded portion of attachment nut 120. The connector end 127 may also be laterally offset from a longitudinal axis, not shown, which extends through the proximal end 122 of the stem 112. The offset placement may be in the medial-lateral direction, the anterior-posterior direction, and virtually at any position between medial-lateral and anterior-posterior.

Referring to FIGS. 6–8B, the femoral component 118 has a pair of condylar portions 136, 138 that are connected by an intercondylar region or boss structure 140. The femoral component 118 has an articulation surface 142 and an opposed surface 143. Further, the femoral component 118 also has an anterior side 152 and a posterior side 154.

The boss structure 140 has a pair of substantially vertical side walls 140A that are generally orthogonal to a top superior surface 140B. The top superior surface 140B is substantially horizontally oriented and extends in the transverse plane. The transverse plane is defined as the horizontal plane that extends through the knee of an upright subject that is orthogonal to both the coronal plane and the sagittal plane as will be appreciated by those having ordinary skill in the art.

The top surface 140B has formed thereon a mounting aperture 147 effective to engage the stem member 112, as discussed in more detail later herein. The boss 140 further has a cavity 146 formed within a bottom inferior surface 140C. An aperture 147 defined by the cavity 146 extends between surfaces 140B, 140C, respectively, of the boss structure 140. As illustrated, the top surface 140B is configured to mate with and engage femoral stem 112.

Figure 7:
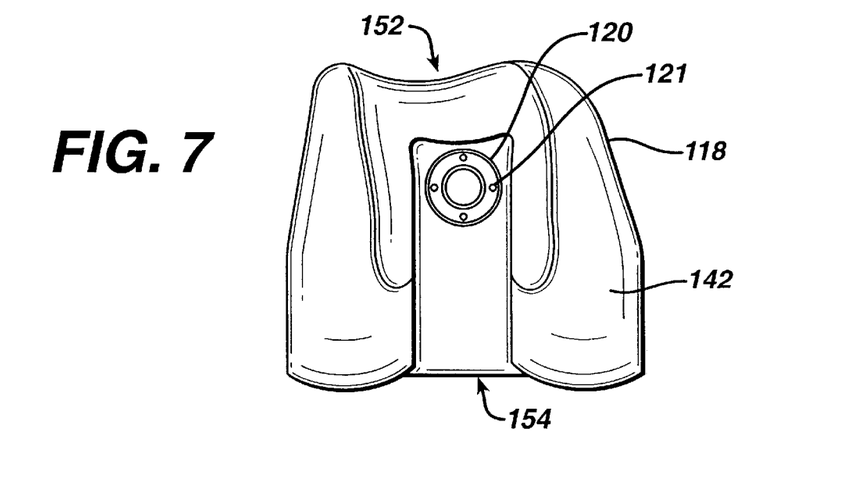
FIG. 7 is a bottom view of the joint component system shown in FIG. 6.
Figure 8A:
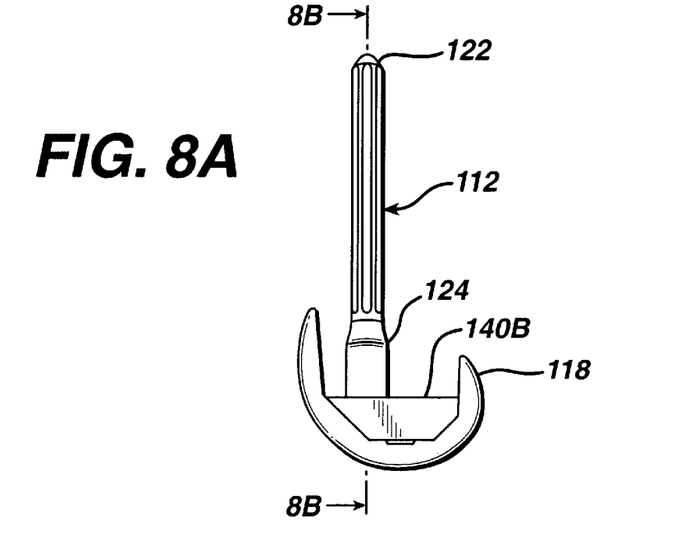
FIG. 8A is a side view of the joint component system shown in FIG.6.
Figure 8B:
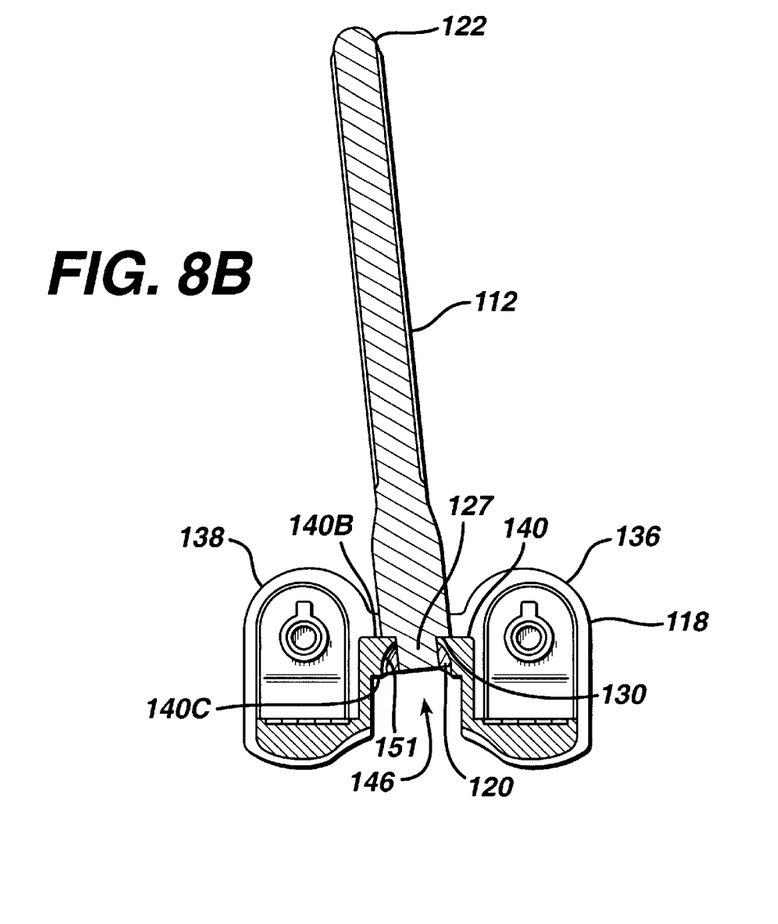
FIG. 8B is a sectional view of the joint component system taken along line 8B—8B in FIG. 8A.

FIGS. 6 and 7 illustrate an attachment nut 120 useful with this embodiment. The nut 120 includes opposed generally horizontal top and bottom surfaces 161, 162 with a generally spherical sidewall 160 extending therebetween. The bottom surface 162 has a series of impressions or indentations 121 formed thereon effective to engage a mounting tool, not shown, used to tighten or loosen the nut 120. A central aperture 164 extends between the top and bottom surfaces 161, 162. Threads are formed within an inner surface of attachment nut 120 to threadably engage the distal connector end 127 of stem 112.

The embodiment as described above may be assembled as follows. The distal end 124 of stem 112 is passed through box aperture 147 such that a portion of the distal end of the stem 112 extends into femoral box cavity 146. The attachment nut 120 is inserted into the boss cavity 146 from the underside of the boss structure to threadably engage the distal connector portion 127 of the stem 112. The threaded connector end 127 of stem 112 threadably engages the threaded attachment nut 120 and fixedly secures the stem 112 to the femoral component 118. In such an engagement, the complementary shape of the cavity endwall 151 and the spherical sidewall 160 of the attachment nut 120 cooperate to position the stem at a selected angle as determined by the boss mounting surface 130. Once the components are assembled, the boss mounting surface 130 of the stem determines the stem angulation. Various offset configurations are also possible utilizing a distal connector portion 127 which is offset from the longitudinal axis extending through the proximal end of the stem as discussed earlier herein.

A variety of modifications and variations of the present invention are possible in light of the above teachings. It is also understood that the basic femoral component construction in the present system can be used for either the right or left knee. All references cited herein are expressly incorporated by reference in their entirety.

What is claimed is:

1. A modular knee prosthesis comprising:
    a first component having a pair of spaced apart condylar portions and a boss structure extending between the condylar portions, the boss structure having a superior mounting surface that extends generally horizontally in a transverse plane and an opposed inferior surface having a cavity formed therein that terminates in a substantially spherically shaped endwall, wherein an aperture extends between the superior mounting and inferior surfaces of the boss structure;
    a second component having a distal mounting surface mountable on the superior mounting surface of the boss structure and a connector portion extending distally from the distal mounting surface and configured to extend through the aperture in the boss structure, the distal mounting surface of the second component and superior mounting surface of the boss structure defining a selected mounting angle therebetween; and an attachment nut matable with the connector portion of the second component for securing the second component to the first component, the attachment nut having a proximal end and a distal end and a spherically shaped outer surface extending from the proximal end to the distal end, the outer surface being shaped for engaging the substantially spherically shaped endwall of the boss structure.

2. The knee prosthesis of claim 1, wherein the second component is an elongate stem.

3. The knee prosthesis of claim 2, wherein at least a portion of the connector portion of the stem is threaded so as to threadably engage the attachment nut.

4. The knee prosthesis of claim 3, wherein the distal end of the stem component is offset a selected distance in the transverse plane relative to the proximal end of the stem.

5. The knee prosthesis of claim 1, wherein the knee prosthesis further comprises a collar having a body portion with an aperture extending therethrough, and wherein the second component is an elongate stem component, the connector portion of the stem component being mountable through the collar aperture and into and through the boss aperture.

6. The knee prosthesis of claim 5, wherein the collar is positionable between the stem component and the boss structure.

7. The knee prosthesis of claim 6, wherein the boss structure includes an anti-rotation means for preventing rotation of the collar when mounted on the boss structure.

8. The knee prosthesis of claim 1, wherein the mounting angle of the mounting surface of the second component is in the range of 1° to about 15° in the medial-lateral direction in the transverse plane, to the medial or lateral side.

9. A modular knee prosthesis comprising:

a femoral component having a pair of spaced apart condylar portions and a boss structure extending between the condylar portions, the boss structure having a superior mounting surface that extends generally horizontally in a transverse plane and an opposed inferior surface having a cavity formed therein that terminates in a substantially spherically shaped endwall, wherein an aperture extends between the superior and inferior surfaces of the boss structure;

a stem component having a proximal end and a distal end, the distal end having a connector portion that is extendable through the aperture in the boss structure;

a collar member mountable on the superior surface of the boss structure, the collar member having a superior and an inferior surface that is substantially transverse to a longitudinal axis of the stem member when mounted thereon, the collar inferior surface and the superior mounting surface of the boss structure defining a selected mounting angle therebetween, the collar member further having an aperture extending between the superior and inferior surfaces; and an attachment nut matable with the connector portion of the stem component for securing the stem member and collar member to the femoral component, the attachment nut having a proximal end and a distal end and a spherically shaped outer surface extending from the proximal end to the distal end, the outer surface being shaped for engaging the substantially spherically shaped endwall of the boss structure.

10. The knee prosthesis of claim 9, wherein the mounting angle of the inferior surface of the collar is in the range of 1° and about 15° in the medial-lateral direction in the transverse plane, to the medial or lateral side.

11. The knee prosthesis of claim 9, wherein the boss structure includes an anti-rotation means for preventing rotation of the collar when mounted on the boss structure.

12. The knee prosthesis of claim 9, wherein at least a portion of the connector portion of the stem component is threaded so as to threadably engage the attachment nut.

13. The knee prosthesis of claim 9, wherein the distal end of the stem component is offset a selected distance in the transverse plane relative to the proximal end of the stem.

14. A modular knee prosthesis comprising:

a femoral component having a pair of spaced apart condylar portions and a boss structure extending between the condylar portions, the boss structure having a top surface that extends generally horizontally in a transverse plane and an opposed bottom surface having a cavity formed therein that terminates in a substantially spherically shaped endwall, wherein an aperture extends between the top and bottom surfaces of the boss structure;

a stem component having a proximal end and a distal end that is mountable through the boss aperture, the distal end of the stem further including a mounting surface which along with the top surface of the boss structure defines a selected mounting angle therebetween; and an attachment nut matable with the distal end of the stem component and having a proximal end and a distal end and a spherically shaped outer surface extending from the proximal end to the distal end, the outer surface being shaped for engaging the spherically shaped endwall of the boss structure for securing the stem member to the femoral component.

* * * * *